United States Patent [19]
Hoffman et al.

[11] Patent Number: 5,744,361
[45] Date of Patent: *Apr. 28, 1998

[54] EXPANSION OF HUMAN HEMATOPOIETIC PROGENITOR CELLS IN A LIQUID MEDIUM

[75] Inventors: Ronald Hoffman; John Brandt, both of Palo Alto, Calif.

[73] Assignee: Indiana University, Bloomington, Ind.

[*] Notice: The term of this patent shall not extend beyond the expiration date of Pat. No. 5,409,825.

[21] Appl. No.: 467,661

[22] Filed: Jun. 6, 1995

Related U.S. Application Data

[63] Continuation-in-part of Ser. No. 226,513, Mar. 31, 1994, and a continuation-in-part of Ser. No. 133,093, Oct. 12, 1993, Pat. No. 5,409,825, which is a continuation-in-part of Ser. No. 682,344, Apr. 9, 1991, abandoned.

[51] Int. Cl.$^6$ ............................ C12N 5/00; A01N 63/00; A01N 65/00
[52] U.S. Cl. ................... 435/372; 435/366; 435/383; 435/384; 435/385; 435/386; 435/404; 435/405; 435/406; 424/937
[58] Field of Search ............................ 435/240.2, 240.3, 435/240.31, 240.1, 325, 366, 372, 383, 384, 385, 386, 387, 404–406; 424/93.7

[56] References Cited

U.S. PATENT DOCUMENTS

| | | | |
|---|---|---|---|
| 4,812,443 | 3/1989 | Takak et al. | 514/143 |
| 4,868,119 | 9/1989 | Clark et al. | 435/360 |
| 5,004,681 | 4/1991 | Hoffman et al. | 435/2 |
| 5,061,620 | 10/1991 | Bukamolo et al. | 435/7.21 |
| 5,073,627 | 12/1991 | Curtis et al. | 530/351 |
| 5,087,570 | 2/1992 | Weissman et al. | 424/93.7 |
| 5,154,921 | 10/1992 | Sager et al. | 424/93.7 |
| 5,199,942 | 4/1993 | Gillis | 604/4 |
| 5,256,560 | 10/1993 | Lawman et al. | 435/325 |
| 5,358,711 | 10/1994 | May et al. | 424/93.7 |
| 5,362,716 | 11/1994 | Kmieak et al. | 514/12 |
| 5,399,493 | 3/1995 | Emerson et al. | 435/172.3 |
| 5,426,098 | 6/1995 | Carlino | 514/12 |
| 5,436,151 | 7/1995 | McGlave et al. | 435/373 |
| 5,437,994 | 8/1995 | Emerson et al. | 435/373 |

OTHER PUBLICATIONS

Brandt et al. (1988) *J. Clin. Invest.* 82:1017–1027 #2 Sep.
Brandt, et al. (1989) *Blood* 74(7) suppl. p. 113a abstract #420.
Brandt, et al. (1990) *J. Clin. Invest* 86:932–941. #3 Sep.
Broxmeyer, et al. (1990) *Exp. Hematology* 18:615, A256. p. 615
Bruno et al. (1989) *Exp. Hematol.* 17:1038–1043.
Eliason et al. (1988) *Exp. Hematol.* 16:307–312.
Gordon et al. (1985) *Exp. Hematol.* 13:937–940.
Gordon et al. (1987) *J. Cell. Physiol.* 130:150–156.
Kobayashi, et al. (1989) *Blood* 73:1836–1841 #7 May.
Lu et al. (1988) *Br. J. Haematol.* 70:149–156. #2.
McNiece et al. (1991) *Exp. Hematol.* 19:226–231.
McNiece et al. (1989) *Blood* 74:609–612 #2 August.
Ponting et al. (1991) *Growth Factors* 4:165–173.
Quesenberry et al. (1991) *J. Cell. Biochem.* 45:273–278.
Roberts et al. (1987) *J. Cell. Physiol.* 132:203–214.
Slovick et al. (1984) *Exp. Hematol.* 12:327–338.
Srour et al. (1991) *Blood Cells* 17:287–295. #2.
Tsai et al. (1986) *Blood* 67: 1418–1426 #5 May.
Verfaillie et al. (1991) *Blood* 77:263–270. #2 Jan.
Robinson et al., The American J. of the Medical Sciences, 300(5): 311–21 (1990).
McNiece et al., Exp. Hiematol., 19:226–31 (1991).
Han, Hokkaido J. Med. Sci, 67(5):674–83 (1990).
Okano et al., ACTA Hematol. Jpn., 53(7):1213–21 (1990).
Heinrich et al., Blood, 82(3): 771–83 (1993).
Ulich et al, Blood, 75(1):48–53 (1990).
Iscove et al, J of Immunology, 145:190–95 (1990).
Robinson et al., The American J. of Medical Sciences, 300(4):237–44 (1990).

*Primary Examiner*—Leon B. Lankford, Jr.
*Assistant Examiner*—Christopher R. Tate
*Attorney, Agent, or Firm*—Pamela J. Sherwood; Bozicevic & Reed LLP

[57] ABSTRACT

The use of individual or combinations of cytokines, particularly IL-3, GM-CSF, and c-kit ligand are employed for long-term hematopoiesis in serum free culture in the absence of stromal cells. The cultures can be used for evaluating compounds and their effect on hematopoiesis, particularly as to lifetime and nature of differentiation. In addition, the expanded cells may be used for engraftment in a mammalian host or enhancement of particular cell lineages in a mammalian host. The subject systems may be used with any mammalian hemopoietic cells, but finds particular application with primates, more particularly humans.

7 Claims, No Drawings

EXPANSION OF HUMAN HEMATOPOIETIC PROGENITOR CELLS IN A LIQUID MEDIUM

CROSS-REFERENCE TO RELATED APPLICATIONS

This application is a continuation in part of application Ser. No. 08/226,513, filed Mar. 31, 1994, and a continuation-in-part of application Ser. No. 08/133,093, filed Oct. 12, 1993, now issued as U.S. Pat. No. 5,409,825, which is a continuation-in-part of application Ser. No. 07/682,344, filed April 9, 1991, now abandoned.

INTRODUCTION

1. Technical Field

The field of this invention is growth and expansion of hematopoietic cells in culture.

2. Background

Mammalian hematopoiesis has been studied in vitro through the use of various long-term marrow culture systems. Dexter and co-workers described a murine system from which CFU-S and CFU-GM could be assayed for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone marrow. Human long-term culture systems were reported to generate assayable hematopoietic progenitor cells for 8 or 9 weeks and longer, frequently up to 20 weeks. Such cultures also relied on the pre-establishment of a stromal cell layer, which is frequently reinoculated with a large, heterogeneous population of marrow cells. Hematopoietic stem cells have been shown to home and adhere to this adherent cell multilayer before generating and releasing more committed progenitor cells. Stromal cells are thought to provide not only a physical matrix on which stem cells reside, but also to produce membrane-contact signals and/or hematopoietic growth factors necessary for stem cell proliferation and differentiation. This heterogeneous mixture of cells comprising the adherent cell layer presents an inherently complex system from which the isolation of discrete variables affecting stem cell growth has proven difficult.

In referring to hematopoietic stem cells, the literature has used the term "stem" to indicate both progenitor cells and the ultimate hematopoietic stem cell. By hematopoietic stem cell, is intended the cell which is capable of long-term regeneration throughout the lifetime of a mammalian host, and is capable of differentiation into all of the different hematopoietic lineages: myelomonocytic, lymphocytic, erythroid, as well as such other cells which are derived from the hematopoietic stem cell. The ultimate hematopoietic stem cell is able to differentiate and mature into all of the individual members of the different lineages. In referring to "stem" cell in the subject application, the term "stem" will be used for the ultimate pluripotent stem cell, while "progenitor cell" will be used to include less primitive cells which are no longer pluripotent yet still immature.

Recently, a study was conducted by McNiece and Langley, which examined the stimulatory effect of c-kit ligand (referred to by the authors as human stem cell factor and by others as stem cell growth factor or mast cell growth factor) on human bone marrow cells alone and in combination with the recombinant human colony stimulating factors: GM-CSF, IL-3 and erythropoietin. The results showed c-kit ligand stimulation of low-density non-adherent antibody depleted CD34+ cells, suggesting that c-kit directly stimulates progenitor cells capable of myeloid and erythroid differentiation.

For many purposes, there is substantial interest in being able to expand hematopoietic stem cells in culture. In providing for bone marrow transplants, it is necessary to provide sufficient numbers of stem cells to engraft the host, where the host has been previously treated to eliminate at least substantially all of the multiplying hematopoietic cells. It is not simply a matter of maintaining cell viability for the stem cells, but also of ensuring that the stem cells increase in numbers without losing their distinctive phenotype. While some success with mammalian stem cells has been achieved in co-culture with stromal cells, it is particularly desirable to grow the hematopoietic stem cells in a culture of known composition, rather than relying upon the presence of other cells for maintenance of the stem cells.

Relevant Literature

Conditions which allow long term in vitro bone marrow culture are described in Dexter et al. (1977) *J. Cell. Physiol.* 91:335–344; Gartner et al. (1980) *P.N.A.S.* 77:4756–4759 and Hocking et al. (1980) *Blood* 56:118–124. Survival of granulocytic progenitors is shown by Slovick et al. (1984) *Exp. Hematol.* 12:327–338. Roberts et al. (1987) *J. Cell. Physiol.* 132:203–214 describes the use of 3T3 cells in such cultures.

Cell surface antigen expression in hematopoiesis is discussed in Strauss, et al. (1983) *Blood* 61:1222–1231 and Sieff et al. (1982) *Blood* 60:703–713. Descriptions of pluripotential hematopoietic cells are found in McNiece et al. (1989) *Blood* 74:609–612 and Moore et al. (1979) *Blood Cells* 5:297–311. Characterization of a human hematopoietic progenitor cell capable of forming blast cell containing colonies in vitro is found in Gordon et al. (1987) *J. Cell. Physiol.* 130:150–156 and Brandt et al. (1988) *J. Clin. Invest.* 82:1017–1027.

Characterization of stromal cells is found in Tsai et al. (1986) *Blood* 67:1418–1426 and Li et al. (1985) *Nature* 316:633–636. The localization of progenitor cells in the adherent layer of cultures is discussed in Coulombel et al. (1983) *Blood* 62:291–297 and Gordon et al. (1985) *Exp. Hematol.* 13:937–940.

Eliason et al. (1988) *Exp. Hematol.* 16:307–312 describes GM-CSF and IL-3 in hematopoiesis. The effect of growth factors in megakaryopoiesis is found in Bruno et al. (1988) *Exp. Hematol.* 16:371–377. McNiece et al (1991) *Exp. Hematol.* 19:226–231 describes the use of stem cell factor in in vitro cultures.

SUMMARY OF THE INVENTION

Long-term cell cultures of stem cell enriched hematopoietic cell fractions are provided by growing the cells in the substantial absence of stromal cells, by including in the culture medium c-kit ligand (MCF), alone or in combination with at least one of the progenitor cell growth supporting factors IL-3, GM-CSF, IL-1, IL-6, or other hematopoietic cell growth factor. The cultures may be grown with or without serum. Long-term cultures are obtained where, by appropriate choice of the factor(s), maintenance and substantial expansion of particular lineages may be achieved.

DESCRIPTION OF THE SPECIFIC EMBODIMENTS

Stromal-free long-term hematopoietic progenitor cell cultures are provided, by growing cell populations enriched for human hematopoietic stem cells (hHSC) in the presence of c-kit ligand (MGF), alone or in combination with at least one of the progenitor cell growth supporting factors IL-3, GM-CSF, G-CSF, IL-1, particularly IL-1α, IL-6, or other growth factors, as appropriate. Extended cultures providing for colony formation can be obtained for at least four weeks, frequently six weeks and in many cases eight weeks or more. By appropriate choice of the various factors, one or more lineages or cell types may be favored in the long-term culture. The culture media that are employed are conventional media for the growth of mammalian cells. Other factors supportive of growth will be added, either by the addition of serum, or by defined factors. However, in the absence of the aforementioned progenitor cell growth factors, the medium is not sufficient to maintain growth for extended periods of time.

The hHSC which are employed may be fresh, frozen, or have been subject to prior culture. They may be fetal, neonate, adult, obtained from fetal liver, bone marrow, blood, particularly G-CSF or GM-CSF mobilized peripheral blood, or any other conventional source. The manner in which the stem cells are separated from other cells of the hematopoietic or other lineage is not critical to this invention. Conveniently, the cells may be separated as described in U.S. Pat. No. 5,061,620. As described, a substantially homogeneous population of hHSC may be obtained by selective isolation of cells free of markers associated with differentiated cells, while displaying epitopic characteristics associated with the stem cells. Usually the population of hHSC will comprise less than about 10% lineage committed cells, more usually less than about 5% lineage committed cells.

The stem cells are characterized by both the presence of markers associated with specific epitopes identified by antibodies and the absence of certain markers as identified by the lack of binding of specific antibodies. At such time as a specific marker is identified for hHSC, binding of an antibody to such marker may provide the desired composition.

A large proportion of the differentiated or lineage committed cells may be removed initially by using a relatively crude separation, where the major cell populations of the hematopoietic system, such as the lymphocytic and myelomonocytic lineages, are removed, as well as minor populations, such as megakaryocytic, mast cells, eosinophils and basophils. Usually, at least about 70 to 90 percent of the hematopoietic cells will be removed. If desired, a prior separation may be employed to remove erythrocytes, by employing ficoll-hypaque separation. The gross separation may be achieved using magnetic beads, cytotoxic agents, affinity chromatography, panning, or the like. Antibodies which find use include antibodies to CD34, or other markers, which allow for a positive selection of stem cells and removal of most mature cells.

Concomitantly or subsequent to the gross separation, a negative selection may be carried out, where antibodies to specific markers present on dedicated cells are employed. For the most part, these markers will include CD2, CD3, CD7, CD8, CD10, CD14, CD15, CD16, CD19, CD20, CD38, CD71 and glycophorin A where combinations comprising at least CD3, CD8, CD10, CD19 and CD20, normally including at least CD14 and CD15 or at least CD2, CD14, CD1 5, CD16, CD19 and glycophorin A are employed. As used herein, Lin⁻ (lineage⁻) refers to a population lacking at least one lineage specific marker. The stem cell population may be further fractionated for HLA-DR negative cells. These combinations of markers used to isolate hHSC may vary as other markers become available.

The hematopoietic cell composition substantially depleted of dedicated cells may then be further separated for Thy-1 positive cells. Exemplary of this stem cell population is a population which is CD34$^+$Thy-1$^+$, preferably CD34$^+$Thy-1$^+$Lin$^-$, CD34$^+$HLA-DR$^-$CD71$^-$ or one which is CD34$^+$ HLA-DR$^-$CD15$^-$, which are highly enriched human hematopoietic stem cell compositions.

The hHSC are then grown in culture in an appropriate liquid nutrient medium comprising a combination of growth factors that are sufficient to maintain the growth of hematopoietic cells. Generally, the seeding level will be at least about 10 cells/ml, more usually at least about 100 cells/ml and generally not more than about $10^5$ cells/ml, usually not more than about $10^4$ cells/ml.

Various media are commercially available and may be used, including Dulbecco's Modified Eagle Medium (DMEM), RPMI, Iscove's medium, etc. The medium may be supplemented with serum, usually fetal bovine serum, generally at a concentration of from about 5–15%, preferably about 10%. Appropriate antibiotics to prevent bacterial growth and other additives, such as pyruvate (0.1–5 mM), glutamine (0.5–5 mM), 2-mercaptoethanol (1–10 ×10$^{-5}$M) may also be included.

Culture in serum-free medium is of particular interest. The medium may be any conventional culture medium, generally supplemented with additives such as iron-saturated transferrin, soy bean lipids, linoleic acid, cholesterol, alphathioglycerol, crystalline bovine haemin, etc., that allow for the growth of hematopoietic cells. The concentrations of growth factors will generally be similar or greater to that employed with serum-containing medium.

Cytokines may be added to the medium individually or in combinations. As combinations, fused proteins may be employed, where the two factors are fused together. The particular order of fusion will not be critical to this invention, so long as the two portions of the molecule act independently and provide for their biological function. The combinations of interest as fused molecules include IL-3 with IL-1α, IL-6 or GM-CSF, particularly IL-3 with GM-CSF.

The following are representative examples of cytokines that may be employed in the present invention. The cytokines may be human in origin, or may be derived from other mammalian species when active on human cells. IL-1 is used in an amount effective to support the cells, generally such amount is at least 1 U/ml and need not exceed 10 U/ml, preferably 2.5 U/ml, where the specific activity is $10^8$ CFU/mg protein. IL-6 is used in an amount effective to support the cells, generally such amount is at least 500 pg/ml and need not exceed 10 ng/ml, preferably 1 ng/ml. IL-3 is used in an amount effective to support the cells, generally such amount is at least 500 pg/ml and need not exceed 2 ng/ml, preferably 500 pg/ml. GM-CSF is used in an amount effective to support the cells, generally such amount is at least 100 pg/ml and need not exceed 1 ng/ml, preferably 200 pg/ml. c-kit ligand (MGF, steel factor, stem cell factor) may be human or murine in origin, preferably human, is used in an amount effective to support the cells, generally such amount is at least 10 ng/ml and need not exceed 500 ng/ml, preferably 10 to 100 ng/ml. Levels in excess of this amount are not detrimental to the cultured cells. FP (fusion protein of IL-3 and GM-CSF as described in Broxmeyer, et al. [1990] Exp. Hematol. 18:615) is used in an amount effective to support the cells, generally such amount is at least 1 ng/ml and need not exceed 25 ng/ml, preferably 10 ng/ml.

Preferably, c-kit ligand (MGF) will be used, alone or in combination with other cytokines, particularly with IL-3 and GM-CSF, where a fusion protein of GM-CSF and IL-3 may be employed. The specific combination of growth factors may be chosen to enhance production of a particular population.

In serum-containing medium, the highest plating efficiency and production of blast cells is seen with c-kit ligand (MGF) alone. The percentage of blast cells in a population may be less than that of the starting population, but will be greater than that of cells cultured without growth factors. The blast cells may be as much as about 50% of the population after 7 days, and as much as about 25% after 14 days. Where a population rich in granulocyte and macrophage progenitors is desired, as evidenced by activity in a CFU-GM assay, a combination of c-kit ligand (MGF) and a fusion protein of GM-CSF and IL-3 is preferable. The number of such active progenitors may be increased as much as about 5–10 fold after three weeks relative to the starting population. For megakaryocyte progenitors, as evidenced by activity in a CFU-MK assay, a combination of of c-kit ligand (MGF) and IL-3, or IL-3/GM-CSF fusion protein is particularly useful. The number of MK active progenitors is increased as much as about 100 fold after two weeks relative to the initial population. For erythrocyte progenitors, as evidenced by activity in a BFU-E assay, a combination of of c-kit ligand (MGF) and IL-3, and optionally erythropoietin, is particularly useful. The number of BFU-E active progenitors may be maintained, or increased relative to the initial population.

Serum-free medium provides for a smaller increase in the number of total cells produced relative to serum containing medium. The combination of factors will generally be sufficient to provide an increase of at least about 5-fold in total cell number over a period of about 28 days, usually an increase of at least about 10 fold, and may be increased as much as about 50-fold. The combination of factors will generally be sufficient to maintain or increase the number of assayable progenitor cells in the culture. The number of assayable progenitor cells may be demonstrated by a number of assays, such as HPP-CFU. The progenitor cell cloning efficiency will usually be at least about 75% that of the starting cell population, more usually 100% that of the starting cell population, and may be as high as 200% that of the starting cell population. The hematopoietic stem cell population will be maintained for several weeks, and may be maintained for 8 weeks or more.

After seeding the culture medium, the culture medium will be maintained under conventional conditions for growth of mammalian cells, generally about 37° C. and 5% carbon dioxide in 100% humidified atmosphere. The factors may be replenished on a daily basis and not less than an a weekly basis, usually from about 2–4 days. Fresh media may be conveniently replaced, in part, by removing a portion of the media and replacing it with fresh media. Usually, not more than about half the media will be removed at any one time, at a frequency of about 4–10 days, preferably about 7 days. In this manner, an effective concentration of the various cytokines may be maintained throughout the life of the culture, the metabolic products which have an adverse affect on the population growth maintained at a low level, and nutrients necessary for growth maintained. Various commercially available systems have been developed for the growth of mammalian cells to provide for removal of adverse metabolic products, replenishment of nutrients, and maintenance of oxygen. By employing these systems, the medium may be maintained as a continuous medium, so that the concentrations of the various ingredients are maintained relatively constant or within a predescribed range. Such systems can provide for enhanced maintenance and growth of the subject cells using the designated media and additives.

After the cells have been expanded to a desired degree, the cells may then be harvested and the aliquot of the cells analyzed for colony forming activity. Normally, these cells will be grown for at least two weeks, usually at least four weeks and may be grown six weeks or more, before harvesting. The total number of cells in culture will usually be increased from about 100 fold after four weeks, and may increased by as much as 1000 fold after four weeks.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for bone marrow transplantation to treat malignancies, bone marrow failure states and congenital metabolic, immunologic and hematologic disorders. Marrow samples will be taken from patients with cancer, and enriched populations of hematopoietic stem cells isolated by means of density centrifugation, counterflow centrifugal elutriation, monoclonal antibody labeling and fluorescence activated cell sorting. The stem cells in this cell population will then be expanded in vitro and will serve as a graft for autologous marrow transplantation. The graft will be infused after the patient has received curative chemo-radiotherapy.

Expanded cell populations can also be utilized for in utero transplantation during the first trimester of pregnancy. Fetuses with metabolic and hematologic disorders will be diagnosed prenatally. Marrow will be obtained from normal individuals and hematopoietic stem cells will be obtained by the methods described previously and expanded in vitro. They will then be administered to the fetus by in utero injection. A chimera will be formed which will lead to partial but clinically significant alleviation of the clinical abnormality.

The harvested cells may be subject to separation, as desired. That is, the cell population enriched for a particular lineage may be further enriched for such lineage by selection using markers associated with a particular lineage, either as progenitors or as mature cells, to provide for a substantially homogenous population. If desired, populations grown with different cytokines may be employed, so as to change the ratios of the various lineages. The cells may be isolated, using various techniques, such as centrifuges, density gradient separations, filtration, or the like, the cells washed free of the media, and then may be used or frozen for subsequent use, in accordance with conventional ways.

The following examples are offered by way of illustration and not by way of limitation.

EXPERIMENTAL

EXAMPLE 1

A. Materials and Procedures

Prior to performing any procedures, informed consent was obtained from all volunteers according to the guidelines of the Human Investigation Committee of the Indiana University School of Medicine.

Cell separation techniques. Bone marrow aspirates were collected from the posterior iliac crests of normal volunteers. Low-density mononuclear bone marrow (LDBM) cells were obtained by density centrifugation of the heparinized marrow over Ficoll-Hypaque (Pharmacia Fine Chemicals, Piscataway, N.J.) at 500 g for 25 min. LDBM cells were suspended in PBS-EDTA (PBS, pH 7.4, containing 5% FBS, 0.01% EDTA wt/vol, and 1.0 g/liter D-glucose) and injected into an elutriator system at 10° C. at a rotor speed of 1,950 rpm using a JA-17 rotor and standard separation chamber (Beckman Instruments, Inc., Palo Alto, Calif.). A fraction of the LDBM eluted at a flow rate of 12–14 ml/min (FR 12–14), enriched for hematopoietic precursors, was collected as described in Brandt, et al. (1988) J. Clin. Invest 82:1017–1027.

Long-term marrow cultures free of stromal cells. Plastic 35-mm tissue culture dishes were seeded with $2\times10^6$ LDBM cells in 1 ml of Iscove's with 10% FBS and $2\times10^{-5}$M methylprednisone. Cultures were incubated at 37° C. in 100% humidified atmosphere containing 5% $CO_2$ in air and fed weekly by total replacement of media. Stromal cells were confluent by 4–6 wk. The stromal cultures were then irradiated with 1,500 rad, the media were replaced, and the cultures were inoculated with $5\times10^3$ sorted bone marrow cells from autologous donors. The media in these cultures were removed at 7–10 d intervals and replaced with fresh media. Suspended, nonadherent cells were then counted and assayed for progenitors.

Long-term suspension cultures. Plastic 35-mm tissue culture dishes containing 1 ml of Iscove's with 10% FBS were inoculated with stromal cell free long-term marrow cells containing $5\times10^3$ cells obtained by sorting and incubated at 37° C. in 100% humidified atmosphere containing 5% $CO_2$ in air. At this time, and every 48 h thereafter, cultures received nothing (1% BSA/PBS), 2.5 U/ml IL-1$\alpha$, 50 U/ml IL-3, 75 U/ml IL-6, 12.5 U/ml GM-CSF, or combinations of the above. At 7 d intervals, cultures were demi-depopulated by removal of one-half the culture volume which was replaced with fresh media. Cells in the harvested media were counted, transferred to slides for staining and morphological examination, and assayed for various progenitor cells.

Hematopoietic growth factors. All cytokines were obtained from the Genzyme Corp., Boston, Mass. Recombinant IL-1$\alpha$ and IL-3 each had a specific activity of $10^8$ CFU/mg protein, while that of IL-6 was $10^7$ and granulocyte/macrophage colony-stimulating factor (GM-CSF) $5\times10^7$ CFCc/mg protein.

Two- and three-color cell sorting. FR 12–14 cells were incubated with mouse monoclonal anti-HPCA-1 (CD34) of the $IgG_1$, subclass (Becton Dickinson Immunocytometry Systems, San Jose, Calif.), washed, and stained with Texas red-conjugated, subclass-specific goat anti-mouse $IgG_1$, (Southern Biotechnology Associates, Inc., Birmingham, Ala.). Cells were next incubated with mouse serum to block any unbound active sites on the second-step antibody. Cells were finally stained with phycoerythrin-conjugated mouse anti-HLA-DR either alone or in combination with FITC-conjugated CD33 (My9, Coulter Immunology, Hialeah, Fla.), CD15 (Leu-M1), or CD71 (transferrin receptor) (Becton Dickinson Immunocytometry Systems). CD15 is present on cells of the granulocytic and monocytic lineages, and an anti-CD15 monoclonal antibody was employed in the hope of eliminating these cellular components from the cell populations (Strauss, et al. [1983] Blood 61:1222–1231). CD71 is present on actively proliferating cells and an anti-CD71 antibody was utilized to separate actively proliferating cells from more quiescent marrow elements (Sieff, et al. [1982] Blood 60:703–713). Controls consisted of the corresponding isotype-matched, nonspecific myeloma proteins used in parallel with staining monoclonal antibodies.

Cells were stained at a concentration of $2\times10^7$/ml and washed after each step in 1% BSA in PBS. A temperature of 4° C. was maintained throughout the procedure.

Immediately after staining, cells were sorted on a Coulter Epics 753 dual-laser flow cytometry system (Coulter Electronics, Inc., Hialeah, Fla.). Texas Red was excited by 590 nm light emitted from a rhodamine 6G dye laser. FITC and phycoerythrin were excited using the 488 nm wavelength from a dedicated 6-W argon laser. Sorting windows were first established for forward angle light scatter (FALS) and Texas red fluorescence. Positivity for each fluorochrome was defined as fluorescence>99% of that of the controls. Cells were next gated on the presence or absence of detectable HLA-DR-phycoerythrin and CD33-FITC, CD15-FITC, or CD71-FITC.

Hematopoietic progenitor cells assays. Cells were suspended at various concentrations in 35-mm plastic tissue culture dishes (Costar Data Packaging, Cambridge, Mass.) containing 1 ml of 30% FBS, $5\times10^{-5}$M 2-mercaptoethanol, 1 U human purified erythropoietin (50 U/mg protein, Toyobo Co. Ltd., Osaka, Japan), 50 U GM-CSF, and 1.1% methylcellulose in Iscove's modified Dulbecco's medium. The cultures were incubated at 37° C. in a 100% humidified atmosphere containing 5% $CO_2$ in air. After 14 d, erythropoietic bursts (BFU-E), granulocyte-macrophage (CFU-GM), and mixed lineage (CFU-GEMM) colonies were scored in situ on an inverted microscope using standard criteria for their identification (Brandt, supra).

High proliferative potential colony-forming cell (HPP-CFC)-derived colonies were enumerated after 28 d in culture according to the recently published criteria of McNiece and co-workers. The human HPP-CFC-derived colony is a late-appearing, very large (0.5 mm or more in diameter) colony composed primarily of granulocytes with a lesser number of monocytes; cell numbers frequently exceed 50,000.

Cells removed from suspension cultures were assayed for CFU-megakaryocyte (CFU-MK) colonies using the serum-depleted method described in detail by Bruno et al. (1988) Exp. Hematol 16:371–377. $5\times10^3$ cells per point were suspended in a 1-ml serum-substituted fibrin clot with 100 U of IL-3 in 35-mm culture dishes and incubated at 37° C. in a 100% humidified atmosphere containing 5% $CO_2$ in air. At 18–24 d, cultures were fixed in situ and stained using rabbit anti-human platelet glycoprotein antisera, and fluorescein-conjugated goat F(ab')$_2$-specific anti-rabbit IgG (Tago, Inc., Burlingame, Calif.) and megakaryocyte colonies were enumerated on a Zeiss fluorescence microscope (Carl Zeiss, Inc., New York, N.Y.). A positive colony was defined as a cluster of three or more fluorescent cells.

B. Experiments

A liquid culture system supplemented with repeated 48-hourly cytokine additions was utilized to study cell populations. In the absence of exogenous cytokines, total cell numbers declined over a 2-week period and assayable CFU-GM persisted for only 1 or 2 wk. The repeated addition of IL-1$\alpha$ did not significantly enhance total cell production or generation of CFU-GM by either CD34+DR$^-$CD15$^-$ or CD34+DR$^-$CD71$^-$ cells. IL-6 did not alter total cell numbers or numbers of assayable CFU-GM in cultures initiated with CD34+DR$^-$CD71$^-$ cells. By contrast, IL-6 increased total cell numbers over seven fold by week 3 by CD34+DR$^-$CD15$^-$ initiated cultures but did not appreciably extend the interval over which CFU-GM were detected. In both sets of experiments, GM-CSF promoted increased total cell production for 6 wk, by which time cell numbers represented 20–80 times the number present in the initial seeding populations. Assayable CFU-GM persisted for 3–4 weeks and cumulatively surpassed those assayable in the initial populations. The single most effective cytokine in terms of promoting cellular expansion, increasing the number of CFU-GM, and lengthening the duration of time over which CFU-GM were assayable was IL-3. Both CD34+DR$^-$CD15$^-$ and CD34+DR$^-$CD71$^-$ cells experienced 200-fold increases in cell numbers by day 28, and, after 1 or 2 weeks in culture, contained equal or slightly greater numbers of CFU-GM than present in the initial inoculi. Assayable progenitors were produced for 4-5 weeks in the system when maintained with IL-3, and viable cell counts remained high at 8 wk. IL-1α or IL-6 prolonged and enhanced these effects when added in combination with IL-3. CFU-GM were assayable after 8 weeks in suspension culture after continued treatment with these two cytokine combinations. No adherent cell layer was established in any of the suspension cultures over the 8-week period of observation.

In a separate experiment, CD34+DR$^-$CD71$^-$ cells were grown in this suspension culture system in the presence of a combination of both IL-3 and IL-6 and assayed for CFU-MK from days 7 through 28 of culture. CFU-MK were detected over this 28 d period. Utilizing this IL-3/IL-6 cytokine combination, the ability of CD34+DR$^-$CD15+ and CD34+DR$^-$CD71+ cells to sustain long-term hematopoiesis was compared to that of the CD34+DR$^-$CD15$^-$ and CD34+DR$^-$CD71$^-$ fractions. Both the CD15-positive and CD71-positive cells failed to generate CFU-GM after 2 wk, and the CD71-positive population, which initially included the overwhelming majority of BFU-E, failed to produce assayable BFU-E after only 7 d in culture.

Morphological analysis of the cells in these suspension cultures during the period of observation revealed changes in the cellular composition of the populations following the addition of various cytokines. IL-1α-and IL-6-containing cultures behaved very similarly to the control samples. Cultures to which no cytokines were added were composed of 90-100% blasts after 1 wk; the CD34+DR$^-$CD15$^-$ cells did not survive 2 weeks in the absence of cytokine whereas the CD34+DR$^-$CD71$^-$ initiated cultures were composed of 40% blasts and 60% monocytes by week 2. Cultures receiving IL-1α had a similar cellular composition. IL-6 facilitated some differentiation to the granulocytic series by both cell populations; the CD34+DR$^-$CD15$^-$ cells produced a significant number of mature granulocytic elements by week 2. GM-CSF, as well as IL-3, reduced the percentage of blasts in these suspension cultures appreciably by day 7. GM-CSF-containing cultures of CD34+DR$^-$CD15$^-$ and CD34+DR$^-$CD71$^-$ cells consisted primarily of metamyelocytes through 4 wks, with a shift to monocytes occurring by week 6.

IL-3 was unique in that, at 3 wks, suspension cultures initiated by either CD34+DR$^-$CD15$^-$ or CD34+DR$^-$CD71$^-$ cells were composed of 48% basophils in the presence of this growth factor. Addition of IL-1α or IL-6 did not alter this trend, all IL-3-containing cultures being composed of about 50% basophils by 3 weeks and retaining significant numbers of basophils throughout the duration of culture.

The cellular composition of hematopoietic colonies assayed from aliquots of the suspension cultures was comparable to those assayed form the original sorted populations with a few notable exceptions. Blast cell colonies, as well as HPP-CFC-derived colonies, were routinely obtained by directly assaying CD34+DR$^-$CD15$^-$ or CD34+DR$^-$CD71$^-$ cells while these colony types were not observed in subsequent clonal assays of cellular aliquots obtained from the long-term liquid cultures. Distribution of GM colony subtypes, however, remained fairly consistent with roughly 40% being granulocyte macrophage, 40% monocyte macrophage, and 20% basophil or eosinophil colonies in either assays initiated with sorted cells of those initiated on days 7 through 42 of liquid culture. These CFU-GM-derived colonies ranged in size from 100 to 2,000 cells with the average colony containing between 200 to 400 cells. After 8 weeks of suspension culture, monocyte macrophage colonies were the predominant colony type observed in the clonal assays.

TABLE I

Total Cell Production of CD34$_+$, DR$^-$, CD15$^-$ Cells after Addition of Various Cytokines

| Cytokine | Day | | | | | | |
|---|---|---|---|---|---|---|---|
| | 0 | 7 | 14 | 21 | 28 | 35 | 42 | 56 |
| | viable cell count × 10$^3$ | | | | | | |
| None | 5 | 1 | 4 | 0 | 0 | 0 | 0 | 0 |
| IL-1* | 5 | 2 | 2 | 0 | 0 | 0 | 0 | 0 |
| IL-3$^+$ | 5 | 53 | 140 | 591 | 1,085 | 533 | 678 | 781 |
| IL-6$^\#$ | 5 | 3 | 4 | 36 | 26 | 16 | 0 | 0 |
| GM-CSF° | 5 | 8 | 14 | 44 | 169 | 213 | 118 | 0 |
| IL-1α/IL-3 | 5 | 32 | 167 | 556 | 1,360 | 1,387 | 758 | 1,069 |
| IL-6/IL-3 | 5 | 47 | 171 | 471 | 854 | 1,440 | 1,200 | 1,216 |

Total cells = cells/ml cultured (½)n, where n = number of previous demi-depopulations.
*2.5 U/ml recombinant human IL-1α were added every 48 h; specific activity 10$^8$ CFU/mg protein.
$^+$50 U/ml recombinant human IL-3 were added every 48 h; specific activity 10$^8$ CFU/mg protein.
$^\#$75 U/ml recombinant human IL-6 were added every 48 h; specific activity 10$^7$ CFU/mg protein.
°12.5 U/ml recombinant human GM-CSF were added every 48 h; specific activity 5 × 10$^7$ CFU/mg protein.

TABLE II

Total Cell production of CD34$^+$, DR$^-$, CD71$^-$ Cells after Addition of Various Cytokines

| Cytokine | Day | | | | | | |
|---|---|---|---|---|---|---|---|
| | 0 | 7 | 14 | 21 | 28 | 35 | 42 | 56 |
| | viable cell count × 10$^3$ | | | | | | |
| None | 5 | 1 | 2 | 0 | 0 | 0 | 0 | 0 |
| IL-1* | 5 | 3 | 0 | 0 | 0 | 0 | 0 | 0 |
| IL-3$^+$ | 5 | 40 | 226 | 964 | 746 | 1,190 | 1,120 | 851 |
| IL-6$^\#$ | 5 | 1 | 2 | 0 | 0 | 0 | 0 | 0 |
| GM-CSF° | 5 | 3 | 34 | 44 | 45 | 445 | 438 | 0 |
| IL-1α/IL-3 | 5 | 23 | 202 | 684 | 1,112 | 835 | 800 | 1,067 |

Total cells = cells/ml cultured (½)n, where n = number of previous demi-depopulations.
*2.5 U/ml recombinant human IL-1α were added every 48 h; specific activity 10$^8$ CFU/mg protein.
$^+$50 U/ml recombinant human IL-3 were added every 48 h; specific activity 10$^8$ CFU/mg protein.
$^\#$75 U/ml recombinant human IL-6 were added every 48 h; specific activity 10$^7$ CFU/mg protein.
°12.5 U/ml recombinant human GM-CSF were added every 48 h; specific activity 5 × 10$^7$ CFU/mg protein.

TABLE III

Total CFU-GM Production by $CD34_+$, $DR^-$, $CD15^-$ Cells after Addition of Various Cytokines

| Cytokine | Week 1 | 2 | 3 | 4 | 5 | 6 | 7 |
|---|---|---|---|---|---|---|---|
| | CFU-GM/ml culture | | | | | | |
| None | 40 | 0 | 0 | 0 | 0 | 0 | 0 |
| IL-1* | 22 | 14 | 0 | 0 | 0 | 0 | 0 |
| IL-3+ | 432 | 696 | 591 | 325 | 0 | 0 | 0 |
| IL-6§ | 42 | 242 | 96 | 0 | 0 | 0 | 0 |
| GM-CSF° | 273 | 200 | 219 | 0 | 0 | 0 | 0 |
| IL-1α/IL-3 | 254 | 397 | 444 | 408 | 139 | 152 | 64 |
| IL-6/IL-3 | 98 | 342 | 236 | 768 | 864 | 1,080 | 384 |

Total CFU-GM = CFU-GM/ml culture (1/2)n, where n = number of previous demi-depopulations.
Cells were seeded at $5 \times 10^3$/ml. CFU-GM in initial (day 0) population = $555/5 \times 10^3$ cells. Colonies grown in methylcellulose containing 50 U/ml GM-CSF and enumerated after 14 d.
*2.5 U/ml recombinant human IL-1α were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE IV

Total CFU-GM Production by $CD34_+$, $DR^-$, $CD71^-$ Cells after Addition of Various Cytokines

| Cytokine | Week 1 | 2 | 3 | 4 | 5 | 6 | 8 |
|---|---|---|---|---|---|---|---|
| | CFU-GM/ml culture | | | | | | |
| None | 15 | 4 | 0 | 0 | 0 | 0 | 0 |
| IL-1α* | 20 | 0 | 0 | 0 | 0 | 0 | 0 |
| IL-3+ | 664 | 272 | 96 | 448 | 119 | 0 | 0 |
| IL-6§ | 51 | 14 | 0 | 0 | 0 | 0 | 0 |
| GM-CSF° | 402 | 360 | 135 | 28 | 0 | 0 | 0 |
| IL-1/IL-3 | 347 | 324 | 342 | 334 | 167 | 240 | 214 |

Total CFU-GM = CFU-GM/ml culture (½)n, where n = number of previous demi-depopulations. Cells were seeded at $5 \times 10^3$/ml. CFU-GM in initial (day 0) population = $690/5 \times 10^3$ cells. Colonies grown in methylcellulose containing 50 U/ml GM-CSF and enumerated after 14 d.
*2.5 U/ml recombinant human IL-1α were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE V

Assayable CFU-MK in Long-Term Suspension Cultures of $CD34^+DR^-CD71^-$ Cells Receiving a Combination of IL-3 and IL-6

| Days in culture* | CFU-MK/ml culture |
|---|---|
| 7 | 42.6 ± 7.6§ |
| 14 | 67.6 ± 56.6 |
| 21 | 17.0 ± 11.8 |
| 28 | 20.2 ± 10.4 |

50 U/ml recombinant human IL-3 were added every 48 h; specific activity $10^8$ CFUc/mg protein. 75 U/ml recombinant human IL-6 were added every 48 h; specific activity $10^7$ CFU/mg protein.
*Cultures were demi-depopulated every 7 d.
+CFU-MK were assayed in serum-free fibrin clot culture containing 100 U/ml IL-3 colonies enumerated at days 18–24 of culture.
§Each point represents the mean ± SD of triplicate assays. Values are not corrected for the effects of demi-depopulated.

TABLE VI

Total CFU-GM and BFU-E Production by Sorted Cell Populations Stimulated with a Combination of IL-3 and IL-6

| Population | Week 1 | 2 | 3 | 4 | 6 | 8 |
|---|---|---|---|---|---|---|
| | CFU-GM (BFU-E) ml culture | | | | | |
| CD34+DR−CD15− | 275(10) | 286(4) | 64 | 32 | 75 | 0 |
| CD34+DR−CD15+ | 7(1) | 26 | 0 | 0 | 0 | 0 |
| CD34+DR−CD71− | 220(5) | 330(4) | 132 | 18 | 43 | 0 |
| CD34+DR−CD71+ | 13 | 16 | 0 | 0 | 0 | 0 |

Total CFU = CFU/ml culture/(½)n = number of previous demi-depopulations.
Cells were seeded at $5 \times 10^3$/ml. 50 U/ml recombinant human IL-3, specific activity $10^8$ CFU/mg protein and 75 U/ml recombinant human IL-6, specific activity $10^7$ CFU/mg protein were added every 48 h. Cells were seeded at $5 \times 10^3$/ml.

TABLE VII

Differential Analysis of $CD34^+$, $DR^-$, $CD15^-$ Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| Control | 7 | 100 | | | | | | | | | |
| IL-1a* | 7 | 100 | | | | | | | | | |
| | 14 | 78 | | | | | | | | | 22 |
| IL-6+ | 7 | 100 | | | | | | | | | |
| | 14 | 27 | 11 | | 9 | | 13 | 38 | | | 2 |
| | 21 | 9 | | | 48 | 2 | 7 | 17 | | | 17 |
| | 28 | | | | 30 | | 4 | | | | 66 |

TABLE VII-continued

Differential Analysis of CD34+, DR−, CD15− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| GM-CSF# | 7 | 25 | 24 | | 27 | 3 | 21 | | | | |
| | 14 | 9 | 1 | | 46 | 3 | 21 | | 13 | | 7 |
| | 21 | 3 | 2 | 1 | 62 | 3 | 5 | | 22 | | 2 |
| | 28 | 6 | | 1 | 43 | 7 | 3 | | 6 | 2 | 32 |
| | 35 | | | 4 | | | | | | | 96 |
| | 42 | | | 1 | | | | | | | 99 |
| IL-3° | 7 | 21 | 44 | | 35 | | | | 1 | | |
| | 14 | 7 | 7 | | 53 | | | | 33 | | |
| | 21 | 8 | | | 44 | | | | 48 | | |
| | 28 | 5 | | | 35 | | 9 | | 35 | | 13 |
| | 35 | 2 | | | 16 | 5 | 20 | | 25 | | 32 |
| | 42 | | | | 15 | | 2 | | 20 | | 63 |
| IL-1α/ | 7 | 1 | 5 | 1 | 53 | 12 | 14 | | 14 | | |
| IL-3 | 14 | 5 | | | 34 | 9 | | | 52 | | |
| | 21 | 1 | | | 53 | 4 | 3 | | 31 | | 8 |
| | 28 | 1 | | | 42 | 12 | 5 | | 32 | | 8 |
| | 35 | | | | 20 | | | | 27 | | 53 |
| | 42 | | | | 8 | | | | 8 | | 84 |
| | 56 | | | | | | | | 11 | | 89 |
| IL-6/IL-3 | 7 | 19 | 26 | 2 | 40 | 5 | 4 | | 4 | | |
| | 14 | 2 | 2 | | 46 | 3 | 1 | | 46 | | |
| | 21 | 5 | 1 | | 37 | 1 | 7 | | 48 | | 1 |
| | 28 | 4 | 1 | | 37 | 10 | 8 | | 35 | | 5 |
| | 42 | 1 | | | 8 | | 1 | | 9 | | 81 |
| | 56 | | | | 2 | | | | 3 | | 95 |

Differential cell counts were performed on Wright-Giemsa stained cytocentrifuge preparations of cells removed from liquid culture. 200 cells per sample were classified; if <200 cells appeared on a slide, all were classified. Abbreviations: Pro, promyelocytes; Myelo, myelocytes; MM, metamyelocytes; Band, neutrophil band form; Seg, segmented neutrophils; Eo, eosinophils; Baso, basophils; E, erythrocytes; and Mo, monocytes.
*2.5 U/ml recombinant human IL-1a were added every 48 h; specific activity $10^8$ CFU/mg protein.
+50 U/ml recombinant human IL-3 were added every 48 h; specific activity $10^8$ CFU/mg protein.
75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE VIII

Differential Analysis of CD34+, DR−, CD71− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| Control | 7 | 90 | | | | | | | | | 10 |
| | 14 | 40 | | | | | | | | | 60 |
| IL-1α* | 7 | 82 | | | | | | | | | 18 |
| IL-6+ | 7 | 43 | 4 | | | | | | | | 13 |
| | 14 | 33 | 20 | | | | | | | | 47 |
| GM-CSF# | 7 | 39 | 33 | | 9 | 5 | 6 | | 5 | | 2 |
| | 14 | 18 | 5 | | 42 | 3 | 12 | | 20 | | |
| | 21 | 4 | | 1 | 66 | 9 | 7 | | | | 4 |
| | 28 | 2 | | | 61 | 3 | 1 | 8 | | | 24 |
| | 35 | 14 | | | 18 | 8 | 8 | 9 | | | 52 |
| | 42 | | | | | | | | | | 100 |
| IL-3° | 7 | 52 | 40 | | 1 | 2 | 2 | | 2 | 1 | |
| | 14 | 29 | 26 | | 26 | 2 | 3 | | 14 | | |
| | 21 | 13 | 4 | 2 | 28 | 2 | 3 | | 48 | | |
| | 28 | 14 | 3 | | 35 | 5 | 1 | | 35 | | 7 |
| | 35 | 9 | | | 20 | 7 | 6 | | 27 | | 31 |
| | 42 | 2 | | | 5 | | 4 | | 16 | 2 | 71 |
| IL-1α/ | 7 | 48 | 42 | | 6 | 2 | 1 | | 2 | | |
| IL-3 | 14 | | 4 | 1 | 53 | 4 | 5 | | 33 | | |
| | 21 | 3 | | | 44 | 1 | 1 | | 49 | | 2 |
| | 28 | 21 | 3 | | 34 | 4 | 3 | 1 | 27 | | 8 |
| | 35 | 3 | | | 23 | 4 | 29 | | 20 | | 21 |

TABLE VIII-continued

Differential Analysis of CD34+, DR−, CD71− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| | 42 | 1 | | | 7 | 3 | 3 | | 16 | | 70 |
| | 56 | | | | | | 1 | | 8 | | 91 |

Differential cell counts were performed on Wright-Giesma stained cytocentrifuge preparations of cells removed from liquid culture. 200 cells per sample were classified; if <200 cells appeared on a slide, all were classified. Abbreviations as in Table VII.
*2.5 U/ml recombinant human IL-1a were added every 48 h; specific activity $10^8$ CFU/mg protein.
⁺50 U/ml recombinant human IL-3 were added every 48 h; specific activity $10^8$ CFU/mg protein.
♯75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

EXAMPLE 2

Long-term bone marrow cultures (LTBMC) were initiated with $5 \times 10^3$ CD34+DR−CD15− marrow cells/ml in plastic 35-mm tissue culture dishes containing 1 ml of Iscove's with 10% FBS and incubated at 37° C. in 100% humidified atmosphere containing 5% $CO_2$ in air. At this time, and every 48 h thereafter, cultures received nothing, or murine mast cell growth factor (MGF; c-kit ligand) alone or in combination with IL-3 or a GM-CSF/IL-3 fusion protein (FP; Broxmeyer, et al. *Exp. Hematol.* 18: 615, 1990). In cultures not receiving cytokines, viable cells were not detectable after two weeks while cultures receiving IL-3, FP, or MGF sustained hematopoiesis for 10 weeks. Addition of IL-3 or FP alone increased cell numbers by 100 fold by day 26, while the combination of MGF and FP expanded cell numbers 1000-fold ($5 \times 10^3$ cells at day 0; $12,500 \times 10^3$ at day 26). Over the 10 week period of LTBMC, treatment with various cytokines led to the following cumulative increases over an input of 213 total assayable hematopoietic progenitor cells (HPC; CFU-GM+BFU-E+CFU-MK): IL-3, 868; FP, 1,265; MGF, 2,006; MGF+IL-3, 4,845; MGF+FP, 155,442. LTBMCs receiving MGF alone possessed a higher HPC cloning efficiency than those receiving IL-3 or FP and its addition increased the cloning efficiencies of cultures containing of IL-3 and FP. The presence of MGF did not increase the longevity of cultures receiving these cytokines.

TABLE IX

Total Cell Production of CD34+, DR−, CD15− Cells after Cytokine Addition

| | Day | |
|---|---|---|
| Cytokine | 0 | 26 |
| | Viable Cell count × $10^3$ | |
| None | 5 | 0 |
| *IL-3 | 5 | 140 |
| ⁺GM-CSF | 5 | 100 |
| °FP | 5 | 1400 |
| MGF | 5 | 520 |
| GM-CSF/IL-3 | 5 | 560 |
| MGF/GM-CSF | 5 | 12,500 |
| MGF/IL-3 | 5 | 1,200 |
| MGF/FP | 5 | 10,000 |

Total cells/ml culture/½Y n = number of previous cell dilutions. Cultures were periodically split to allow for cellular expansion and to perform several analyses at different time points.
*500 pg/ml recombinant human IL-3 was added every 48 hours.
⁺200.0 pg/ml recombinant human GM-CSF was added every 48 hours.
°10.0 ng/ml of recombinant GM-CSF-IL-3 fusion protein was added each day.
100.0 ng/ml of murine recombinant mast cell growth factor (MGF) was added every 48 hours.

TABLE X

Differential Analysis of $CD34_+$, $DR^-$, $CD15^-$ Cells After Addition of Various Cytokines on Day 26 of Suspension Culture

| Cytokine | Blasts | Pro | Myelo | MM | Band | Seg | Lymph | Eo | Baso | Mo | Norm |
|---|---|---|---|---|---|---|---|---|---|---|---|
| FP | 3 | 7 | 9 | 9 | 27 | 3 | 5 | 2 | 9 | 0 | 5 |
| GM-CSF/IL-3 | 1 | 7 | 4 | 13 | 24 | 32 | 4 | 3 | 4 | 0 | 0 |
| MGF | 32 | 4 | 9 | 9 | 13 | 12 | 7 | 1 | 1 | 12 | 0 |
| MGF/GM-CSF | 21 | 10 | 15 | 12 | 14 | 7 | 5 | 2 | 3 | 11 | 0 |
| MGF/IL-3 | 38 | 3 | 15 | 12 | 13 | 4 | 2 | 2 | 4 | 7 | 2 |
| MGF/FP | 37 | 17 | 16 | 9 | 9 | 5 | 1 | 0 | 6 | 0 | 5 |

Differential cell counts were performed on Wright Giemsa stained cytocentrifuge preparations of cells removed from liquid culture. 200 cells per sample. Abbreviation used, Norm, normoblasts, other abbreviations as in Table VII. Cytokines were added at same dose as detailed in legend of Table I.

EXAMPLE 3

Liquid culture systems supplemented with repeated 48-hourly cytokine additions were utilized to study cell populations cultured from two donors. In the absence of exogenous cytokines, total cell numbers declined over a 1 to 2-week period and assayable CFU-GM persisted for only a 1 to 2-week period. In donor 1, MGF/FP cytokine combination promoted increased total cell production for 8 weeks, by which time cell numbers represented over $110 \times 10^3$ times the number present in the initial seeding populations. In donor 2 the same cytokine combination promoted increased total cell production for 6 weeks, by which time the cell numbers represented by over $16 \times 10^3$ times the number present in the initial seeding population. Assayable CFU-GM for donor 1 and donor 2 cultured with MGF/FP cytokine combination persisted for 6-8 weeks and 3-4 weeks, respectively and significantly surpassed the CFU-GM population initially assayable.

The cytokine combination MGF/IL-3 promoted over $2 \times 10^3$ fold increase in total cell production over the initial seeding for donor 1 at 6 weeks and donor 2 at 8 weeks. Additionally, viable cell counts remain high through 10 weeks. The assayable expansion of CFU-GM for donor 1 and 2 cultured with MGF/IL-3 cytokine combination persisted for 6-8 weeks for each donor and each significantly surpassed the CFU-GM population assayable initially.

Total BFU-E production by $CD34+DR-CD15^-$ cells was assayed. In donor 1 and donor 2 the cytokine combination MGF/FP persisted for 1-2 weeks and 3-4 weeks, respectively with only donor 2 showing a significant increase over the BFU-E population initially assayable. The cytokine combination MGF/IL-3 persisted in donor 1 for 2-3 weeks and in donor 2 for 3-4 weeks, with both showing significant increase in weeks 1-2 over the BFU-E population initially assayable.

The cytokine combination of MGF/IL-3 for both donors 1 and 2 show CFU-MK persistence for through 10 weeks and each has significantly surpassed the initially assayable CFU-MK population. Donors I and 2 show CFU-MK persistence for 6-8 weeks and 8-10 weeks, respectively, both showing significant increases over the initial CFU-MK population.

Morphological analysis of the cells in the suspension cultures of donor 1 during the period of observation revealed changes in the cellular composition of the population following the addition of various cytokines. Cultures receiving MGF/FP were composed of 11% blasts by 14 days and cultures receiving MGF/IL-3 were composed of 17% blasts by 14 days. The highest percentage of blasts by 14 days was in the cultures receiving MGF alone which were composed of 30% blasts. In contrast IL-3 and FP containing cultures had reduced the percentage of blasts cells appreciably by day 14.

Although MGF percentages are high, the overall expansion of cultures receiving MGF is not as substantial as with other combinations. However the cultures receiving MGF/IL-3 cytokines provide high plating percentages and substantial overall expansion.

TABLE XI

Total Cell Production of $CD34_+DR^-CD15^-$ Cells Cultured in the Presence of Various Cytokines
viable cell count $\times 10^3$/ml

| Cyto- | Week | | | | | | |
|---|---|---|---|---|---|---|---|
| kine | 1 | 2 | 3 | 4 | 6 | 8 | 10 |
| Donor 1 | | | | | | | |
| None | 1 | 0 | 0 | 0 | 0 | 0 | 0 |
| IL-3[1] | 28 | 144 | 271 | 560 | 480 | 762 | 960 |
| GM-CSF[2] | 12 | 107 | 436 | 1,085 | 2,680 | 2,080 | 1,760 |
| IL-3/GM-CSF | 23 | 244 | 742 | 1,620 | 1,979 | 2,035 | 2,720 |
| FP[3] | 42 | 262 | 587 | 1,240 | 3,000 | 1,494 | 480 |
| MGF[4] | 8 | 104 | 933 | N.D.[5] | 1,680 | 1,760 | 640 |
| MGF/FP | 101 | 1,211 | 35,100 | 101,000 | 262,400 | 550,000 | 100,000 |
| MGF/IL-3 | 38 | 213 | 978 | 2,820 | 10,800 | 5,680 | 5,120 |
| Donor 2 | | | | | | | |
| None | 1 | 0 | 0 | 0 | 0 | 0 | 0 |
| IL-3 | 24 | 180 | 650 | 605 | 1,400 | 960 | 864 |
| FP | 41 | 810 | 2,100 | 6,680 | 1,840 | 4,320 | 5,280 |
| MGF | 8 | 27 | 71 | 98 | 230 | 70 | 0 |
| MGF/FP | 100 | 1,280 | 15,700 | 6,400 | 81,000 | 19,520 | 0 |
| MGF/IL-3 | 36 | 305 | 780 | 1,380 | 6,960 | 10,400 | 5,440 |
| Donor 3 | | | | | | | |
| MGF/FP | N.D. | 5,040 | 14,460 | 14,800 | 8,960 | | |

Total cells = cells/ml culture/$(\frac{1}{2})^n$ where n = number of previous demidepopulations.

TABLE XI-continued

Total Cell Production of CD34+DR-CD15- Cells Cultured in the Presence of Various Cytokines
viable cell count × $10^3$/ml

| Cyto-kine | Week 1 | 2 | 3 | 4 | 6 | 8 | 10 |
|---|---|---|---|---|---|---|---|

Cultures were seeded at 5 × $10^3$ cells/ml.
[1] 500 pg/ml recombinant human IL-3 was added every 48 hours; specific activity 3.5 × $10^8$ CFU/mg protein.
[2] 250 pg/ml recombinant human GM-CSF was added every 48 hours; specific activity 2 × $10^8$ protein.
[3] 10 ng/ml recombinant human FP was added every 48 hours; specific activity 1–2 × $10^8$ CFU/mg protein.
[4] 50 ng/ml recombinant murine MGF was added every 48 hours; specific activity $10^6$ CFU/mg protein.
[5] N.D. = not determined.

TABLE XII

Differential Analysis of CD34+DR-CD15- Cells Following Culture with Various Cytokines

| Cytokine | Day | Blast % | Pro | Myelo | Meta | Band | Seg | Baso | Eos | Mono |
|---|---|---|---|---|---|---|---|---|---|---|
| Post Sort | 0 | 82 | 1 | 1 | | | | 6 | | 10 |
| IL-3[1] | 7 | 10 | 8 | 16 | 2 | | 9 | 50 | 2 | 3 |
| | 14 | 2 | 4 | 39 | 4 | 3 | 10 | 28 | | 10 |
| | 28 | 3 | 6 | 13 | 3 | 1 | 6 | 61 | | 7 |
| FP[2] | 7 | 10 | 21 | 52 | 5 | | 2 | 7 | | 3 |
| | 14 | 1 | 4 | 17 | 8 | 3 | 20 | 14 | | 33 |
| | 28 | | 1 | 24 | 7 | 4 | 36 | 8 | | 20 |
| MGF[3] | 7 | 54 | 39 | 3 | | | | 1 | | 3 |
| | 14 | 30 | 38 | 9 | 1 | 1 | 1 | | | 20 |
| | 28 | 1 | 7 | 21 | 18 | 13 | 15 | 1 | 1 | 23 |
| MGF/FP | 7 | 29 | 22 | 23 | 3 | | 4 | 18 | | 1 |
| | 14 | 11 | 22 | 16 | 4 | 2 | 4 | 13 | | 28 |
| | 28 | 1 | 8 | 13 | 12 | 2 | 10 | 2 | | 52 |
| MGF/IL-3 | 7 | 31 | 15 | 48 | | | 2 | 4 | | |
| | 14 | 17 | 14 | 9 | 2 | 4 | 8 | 34 | | 12 |
| | 28 | | 8 | 46 | 17 | 2 | 17 | 2 | | 8 |

Differential cell counts were performed on Wright-Giemsa-stained cytocentrifuge preparations of cells removed from liquid culture. ≧100 cells per sample were classified. Abbreviations: Pro, promyelocyte; Myelo, myelocyte; Meta, metamyelocyte; Band, neutrophil band form; Seg, segmented neutrophil; Baso, basophil; Eos, eosinophil; Mono, monocyte.
[1] 500 pg/ml recombinant human IL-3, specific activity 3.5 × $10^8$ CFU/mg protein.
[2] 10 ng/ml recombinant human FP, specific activity 1–2 × $10^8$ CFU/mg protein.
[3] 50 ng/ml recombinant murine MGF, specific activity $10^6$ CFU/mg protein.

TABLE XIII

Total CFU-GM Production by CD34+DR-CD15- Cells Cultured in the Presence of Various Cytokines
CFU-GM/ml culture[1]

| Cytokine | Week 1 | 2 | 3 | 4 | 6 | 8 |
|---|---|---|---|---|---|---|
| *Donor 1* | | | | | | |
| None | 8 | 0 | 0 | 0 | 0 | 0 |
| IL-3[2] | 132 | 28 | 80 | N.D.[5] | N.D. | 128 |
| GM-CSF[3] | 192 | 112 | 88 | N.D. | 128 | 0 |
| IL-3/GM-CSF | 196 | 104 | 36 | N.D. | 128 | 576 |
| FP[4] | 86 | 112 | 128 | 176 | N.D. | 64 |
| MGF[5] | 290 | 396 | 608 | 448 | 96 | 0 |
| MGF/FP | 376 | 1,600 | 14,800 | 58,000 | 80,000 | 0 |
| MGF/IL-3 | 144 | 348 | 104 | 416 | 2,528 | 192 |
| *Donor 2* | | | | | | |
| None | 0 | 0 | 0 | 0 | 0 | N.D. |
| IL-3 | 232 | 196 | 96 | 16 | 64 | N.D. |
| FP | 84 | 148 | 288 | 320 | 544 | N.D. |
| MGF | 106 | 152 | 360 | 64 | 128 | N.D. |
| MGF/FP | 114 | 1,440 | 10,600 | N.D. | N.D. | N.D. |
| MGF/IL-3 | 62 | 240 | 504 | 32 | 1,024 | N.D. |
| *Donor 3* | | | | | | |
| MGF/FP | N.D. | 12,448 | 32,936 | 32,264 | 1,254 | 0 |

Total CFU-GM = CFU-GM/ml culture/(½)n where n = number of previous demidepopulations.

[1] Cultures were seeded at 5 × $10^3$ cells/ml. CFU-GM/5 × $10^3$ cells in initial population: Donor 1, 150; Donor 2, 227; Donor 3, 144. Colonies grown in methylcellulose containing 500 pg/ml GM-CSF and 1 U human urinary erythropoietin and enumerated after 14 days.
[2] 500 pg/ml recombinant human IL-3 was added every 48 hours; specific activity 3.5 × $10^8$ CFU/mg protein.
[3] 250 pg/ml recombinant human GM-CSF was added every 48 hours; specific activity 2 × $10^8$ CFU/mg protein.
[4] 10 ng/ml recombinant human FP was added every 48 hours; specific activity 1–2 × $10^8$ CFU/mg protein.
[5] 50 ng/ml recombinant murine MGF was added every 48 hours; specific activity $10^6$ CFU/mg protein.
[6] N.D. - not determined.

TABLE XIV

Total BFU-E Production by CD34+DR−CD15− Cells Cultured in the Presence of Various Cytokines
BFU-E/ml culture[1]

| Cytokine | WEEK 1 | 2 | 3 | 4 |
|---|---|---|---|---|
| *Donor 1* | | | | |
| None | 0 | — | — | — |
| IL-3 | 24 | 0 | 0 | 0 |
| GM-CSF | 8 | 0 | 0 | 0 |
| IL-3/GM-CSF | 22 | 4 | 0 | 0 |
| FP | 20 | 4 | 0 | 0 |
| MGF | 8 | 40 | 0 | 0 |
| MGF/FP | 98 | 0 | 0 | 0 |
| MGF/IL-3 | 238 | 4 | 0 | 0 |
| *Donor 2* | | | | |
| Control | 0 | — | — | — |
| IL-3 | 40 | 28 | 0 | 0 |
| FP | 132 | 68 | 56 | 16 |
| MGF | 6 | 0 | 0 | 0 |
| MGF/FP | 662 | 100 | 200 | 0 |
| MGF/IL-3 | 1,062 | 272 | 40 | 0 |

Total BFU-E = BFU-E/ml culture/($\frac{1}{2}$)$^n$ where number of previous demidepopulations.
[1] Cultures were seeded at $5 \times 10^3$ cells/ml. Each point represents the mean of two separate experiments. Mean BFU-E/5 × 10³ cells in initial population: = Donor 1, 173; Donor 2, 154. Colonies grown in methylcellulose containing 500 pg/ml GM-CSF and 1 U human urinary eryLhropoietin and enumerated after 12 days.
[2] 500 pg/ml recombinant human IL-3 was added every 48 hours; specific activity $3.5 \times 10^8$ CFU/mg protein.
[3] 250 pg/ml recombinant human GM-CSF was added every 48 hours; specific activity $2 \times 10^8$ CFU/mg protein.
[4] 10 ng/ml recombinant human FP was added every 48 hours; specific activity $1–2 \times 10^3$ CFU/mg protein.
[5] 50 ng/ml recombinant murine MGF was added every 48 hours; specific activity $10^6$ CFU/mg protein.

TABLE XV

Total CFU-MK Production by CD34+DR−CD15− Cells Cultured in the Presence of Various Cytokines
CFU-MK/ml culture[1]

| Cytokine | 2 | 3 | 4 | 6 | 8 | 10 |
|---|---|---|---|---|---|---|
| *Donor 1* | | | | | | |
| None | 0 | 0 | 0 | 0 | 0 | 0 |
| IL-3[2] | 14 | 74 | 100 | 118 | 48 | N.D.[5] |
| GM-CSF[3] | 12 | 40 | 20 | 48 | 32 | 0 |
| IL-3/GM-CSF | 20 | 80 | 96 | 120 | N.D. | N.D. |
| FP[4] | 28 | 120 | 184 | 118 | 96 | 64 |
| MGF[5] | 6 | 12 | 36 | 20 | 0 | 0 |
| MGF/FP | 40 | 120 | 120 | 120 | N.D. | 0 |
| MGF/IL-3 | 26 | 90 | 208 | 220 | 128 | 64 |
| *Donor 2* | | | | | | |
| None | 8 | 0 | 0 | 0 | 0 | 0 |
| IL-3 | 26 | 100 | 140 | 140 | 64 | 64 |
| GM-CSF | 24 | 40 | 60 | 80 | 32 | 0 |
| IL-3/GM-CSF | 40 | 120 | 160 | 200 | 64 | 64 |
| FP | 56 | 120 | 200 | 200 | 96 | 64 |
| MGF | 10 | 36 | 60 | 60 | 0 | 0 |
| MGF/FP | 56 | 200 | 200 | 200 | 40 | 0 |
| MGF/IL-3 | 34 | 120 | 240 | 260 | 160 | 192 |

Total CFU-MK = CFU-MK/ml culture/($\frac{1}{2}$)$^n$ where n = number of previous demidepopulations.
[1] Cultures were seeded at $5 \times 10^3$ cells/ml. Each point represents the mean of two separate experiments. Mean CFU-MK/5 × 10³ cells in initial populations = 0. Colonies cultured in fibrin clot containing 1 ng IL-3 and enumerated at 15 days.
[2] 1 ng/ml recombinant human IL-3 was added every 48 hours; specific activity $3.5 \times 10^8$ CFU/mg protein.
[3] 200 pg/ml recombinant human GM-CSF was added every 48 hours; specific activity $2 \times 10^8$ CFU/mg protein.
[4] ng/ml recombinant human FP was added every 48 hours; specific activity $1–2 \times 10^8$ CFU/mg protein.
[5] 100 ng/ml recombinant murine MGF was added every 48 hours; specific activity $10^8$ CFU/mg protein.
[6] N.D. - not determined.

TABLE XVI

Plating Efficiency of CD34+ DR− CD15− Cells Cultured in the Presence of Various Cytokines

| Cytokine | 1 | 2 | 3 | 4 | 6 | 8 |
|---|---|---|---|---|---|---|
| | % Plating Efficiency[1] | | | | | |
| None | N.D.[6] | — | — | — | — | — |
| IL-3[2] | 0.86 | 0.072 | 0.023 | 0.003 | 0.005 | 0.009 |
| GM-CSF[3] | 1.67 | 0.105 | 0.020 | N.D. | 0.005 | 0.000 |
| IL-3/GM-CSF | 0.96 | 0.044 | 0.005 | N.D. | 0.006 | 0.028 |
| FP[4] | 0.42 | 0.039 | 0.019 | 0.010 | 0.015 | 0.002 |
| MGF[5] | 2.58 | 0.493 | 0.580 | 0.065 | 0.031 | 0.000 |
| MGF/FP | 0.65 | 0.127 | 0.056 | 0.029 | 0.015 | 0.000 |
| MGF/IL-3 | 2.10 | 0.173 | 0.041 | 0.008 | 0.019 | 0.002 |

[1] % Plating Efficiency = colonies enumerated/cells cultured × 100%. Cells at each timepoint were counted and cultured in methylcellulose containing 500 pg GM-CSF and 1 U human urinary erythropoietin or in fibrin clot containing 1 ng IL-3 and enumerated at 14 days. Each point represents the mean of two to four separate experiments. Mean cloning efficiency of initial (day 0) population: 4.54%.
[2] 500 pg/ml recombinant human IL-3 was added every 48 hours; specific activity $3.5 \times 10^8$ CFU/mg protein.
[3] 200 pg/ml recombinant human GM-CSF was added every 48 hours; specific activity $2 \times 10^8$ CFU/mg protein.
[4] 10 ng/ml recombinant human FP was added every 48 hours; specific activity $1–2 \times 10^8$ CFU/mg protein.
[5] 100 ng/ml recombinant murine MGF was added every 48 hours; specific activity $10^8$ CFU/mg protein.
[6] N.D. - not determined.

EXAMPLE 4

Serum-free long-term suspension human bone marrow culture system. Serum free liquid culture system media was prepared as described by Ponting, et al. (1991) *Growth Factors* 4:165–173. Both serum free and serum containing cultures were initiated with CD34+DR− CD15− cells, and supplemented every 48 hours with 100 ng/ml of c-kit ligand (MGF) and 10 ng/ml of FP.

As shown in Table I, cultures maintained in serum-free media were characterized by far less total cell production than has been observed in comparable serum containing cultures. Over six weeks of observation, these cultures only increased total cell number by 24-fold. However, the progenitor cell cloning efficiency in serum-free cultures was 1.4% after 28 days of LTBMC, in comparison to a cloning efficiency of 0.03% in comparable serum-containing cultures. These studies suggest that the serum-free culture system is preferable for expanding progenitor cell numbers at the expense of impairing the production of more differentiated cells.

TABLE XVII

Plating Efficiency of CD34+DR−CD15− Cells Cultured in Serum-Free Medium*

| Days in Culture | Cell no. × 10³ | Progenitor Cells | |
|---|---|---|---|
| | | CFU-GM | HPP-CFC |
| 0 | 10 | 375 | 40 |
| 14 | 30 | 744 | 9 |
| 28 | 70 | 1,050 | 21 |
| 42 | 140 | 140 | 42 |

CD34+DR−CD15− cells were suspended in serum-free medium and supplemented with 100 ng/ml of c-kit ligand (MGF) and 10 ng/ml of FP every 48 hours.

It is evident from the above results, that substantial cell expansions may be obtained from hematopoietic progentor cells in the substantial or complete absence of stromal cells and/or serum. These cultures may be grown and maintained for extended periods of time, where progenitor cells are able to expand and maintain the culture. Disadvantages associated with the presence of stromal cells, the lack of a controlled system dependent upon the nature and activity of the stromal cells, is avoided by using factors individually or in combination. In this manner, substantial expansions of hematopoietic cells from a limited number of progenitors can be achieved in a controlled substantially reproducible manner.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of culturing human hematopoietic stem cells, the method comprising:

culturing an initial population of human hematopoietic stem cells comprising less than 10% lineage committed cells in a serum-free, liquid culture medium comprising at least about 10 ng/ml of mast cell growth factor; wherein said medium is free of stromal cells and comprises at least one cytokine selected from the group consisting of interleukin 3 at a concentration of at least about 500 pg/ml, granulocyte macrophage colony stimulating factor at a concentration of at least about 100 pg/ml and IL-3/GM-CSF fusion protein at a concentration of at least about 1 ng/ml;

wherein during said culturing the number of assayable human hematopoietic stem cells is maintained or increased.

2. The method according to claim 1, wherein said at least one cytokine is added to said culture medium every 48 hours.

3. The method according to claim 1, wherein said human hematopoietic stem cells are CD34+.

4. The method according to claim 3, wherein said human hematopoietic stem cells are Lin−.

5. The method according to claim 4, wherein said Lin− cells are lacking at least one of CD14, CD15, CD71, or HLA-DR.

6. The method according to claim 2, wherein said human hematopoietic stem cells are CD34+Thy-1+lin−.

7. The method according to claim 2, wherein said at least one cytokine is IL-3/GM-CSF fusion protein.

* * * * *